(12) United States Patent
Martinez-Luna et al.

(10) Patent No.: US 10,869,773 B2
(45) Date of Patent: Dec. 22, 2020

(54) PROSTHETIC FINGERTIP END EFFECTORS

(71) Applicant: College Park Industries, Inc., Warren, MI (US)

(72) Inventors: Carlos Humberto Martinez-Luna, Boylston, MA (US); Michael Alfred Delph, II, Port Jefferson Station, NY (US); Taylor Raven Duckworth, Merrimack, NH (US); Todd Richard Farrell, Waltham, MA (US); Thane Robert Hunt, Colchester, CT (US); Craig Malone Kelly, Dracut, MA (US); Kevin Edward Keough, Sharon, MA (US); Carlton Winslow King, Westfield, MA (US); Benjamin Douglas Pulver, Naples, NY (US); Todd William Roberts, Saint Inigoes, MD (US); Benjamin Edward McDonald, Holliston, MA (US)

(73) Assignee: College Park Industries, Inc., Warren, MI (US)

( * ) Notice: Subject to any disclaimer, the term of this patent is extended or adjusted under 35 U.S.C. 154(b) by 99 days.

(21) Appl. No.: 16/156,722

(22) Filed: Oct. 10, 2018

(65) Prior Publication Data

US 2019/0105184 A1 Apr. 11, 2019

Related U.S. Application Data

(60) Provisional application No. 62/669,746, filed on May 10, 2018, provisional application No. 62/570,184, filed on Oct. 10, 2017.

(51) Int. Cl.
*A61F 2/58* (2006.01)
*A61F 2/50* (2006.01)
(Continued)

(52) U.S. Cl.
CPC ............ *A61F 2/586* (2013.01); *A61F 2/5044* (2013.01); *A61F 2/588* (2013.01); *A61F 2/68* (2013.01);
(Continued)

(58) Field of Classification Search
CPC ........ A61F 2/586; A61F 2/5044; A61F 2/588; A61F 2/68; A61F 2/72; A61F 2002/587; A61F 2002/6854; A61F 2002/6872
(Continued)

(56) References Cited

U.S. PATENT DOCUMENTS 2,429,866 A 10/1947 Broste
4,332,038 A * 6/1982 Freeland ................. A61F 2/588
623/64

(Continued)

FOREIGN PATENT DOCUMENTS

GB 1389233 A 4/1975
WO 2008088204 A1 7/2008

OTHER PUBLICATIONS

Web page for Bebionic artificial hand; URL: http://bebionic.com/the_hand/grip_patterns/; located on the Internet on Sep. 11, 2018.
(Continued)

*Primary Examiner* — Suba Ganesan
*Assistant Examiner* — Aren Patel
(74) *Attorney, Agent, or Firm* — Dinsmore & Shohl LLP

(57) ABSTRACT

A prosthetic finger includes a main body and a terminal gripper at an end of the main body for enabling fine-motor grasping skills. The terminal gripper has at least two tongs movable relative to one another. The prosthetic finger includes a gripping mode and a flexion mode. In the gripping mode, the tongs of the terminal gripper are able to move relative to one another while the main body is not able to flex, and in the flexion mode, the main body is able to flex
(Continued)

while the at two tongs is not able to move relative to one another.

30 Claims, 22 Drawing Sheets

(51) Int. Cl.
*A61F 2/72* (2006.01)
*A61F 2/68* (2006.01)
(52) U.S. Cl.
CPC ........ *A61F 2/72* (2013.01); *A61F 2002/6854* (2013.01); *A61F 2002/6872* (2013.01)
(58) Field of Classification Search
USPC .................................................... 623/57–65
See application file for complete search history.

(56) References Cited

U.S. PATENT DOCUMENTS

| | | |
|---|---|---|
| 6,921,419 B2 | 7/2005 | Weir et al. |
| 8,840,160 B2 | 9/2014 | Caron L'Ecuyer et al. |
| 8,920,519 B2 | 12/2014 | Johannes et al. |
| 9,579,219 B2 | 2/2017 | Amend, Jr. et al. |
| 9,629,731 B2 | 4/2017 | Thompson, Jr. et al. |
| 2010/0042229 A1 | 2/2010 | Hawk |
| 2012/0150321 A1* | 6/2012 | Goldfarb ................. A61F 2/583 623/57 |
| 2015/0021947 A1 | 1/2015 | Veatch |
| 2016/0367383 A1 | 12/2016 | Sensinger et al. |
| 2017/0014246 A1 | 1/2017 | Veatch |
| 2018/0311827 A1* | 11/2018 | Bicchi ..................... A61F 2/583 |

OTHER PUBLICATIONS

Web page for Naked Prosthetics PIPDriver located on the Internet on Sep. 11, 2018 at URL https://www.npdevices.com/pipdriver.

Web page for System Electric Greifer DMC VariPlus located on the Internet on Sep. 11, 2018 at URL https://professionals.ottobockus.com/Prosthetics/Upper-Limb-Prosthetics/Myo-Hands-and-Components/Myo-Terminal-Devices/System-Electric-Greifer-DMC-VariPlus/p/8E34~59-1.

Web page for MyoHand VariPlus Speed located on the Interner on Sep. 11, 2018 at URL https://professionals.ottobockus.com/Prosthetics/Upper-Limb-Prosthetics/Myo-Hands-and-Components/Myo-Terminal-Devices/MyoHand-VariPlus-Speed/p/8E38~59-R7%201~24.

Web page for Touch Bionics Motion Control ETD located on the Internet on Sep. 11, 2018 at URL https://www.touchbionics.com/products/motion-control-etd.

Web page for Touch Bionics i-limb located on the Internet on Sep. 11, 2018 at URL http://touchbionics.com/products/how-i-limb-works.

* cited by examiner

PROSTHETIC FINGERTIP END EFFECTORS

CROSS REFERENCE

This application claims priority from U.S. Provisional Application No. 62/669,746 filed May 10, 2018 and 62/570,184 filed Oct. 10, 2017 the entire content of which are incorporated herein by reference.

GOVERNMENT SUPPORT

This invention was made with government support under 1R43HD090800-01 awarded by The National Institutes of Health: Eunice Kennedy Shriver National Institute of Child Health & Human Development. The government has certain rights in the invention. 37 CFR 401.14(f)(4).

FIELD OF THE INVENTION

The present invention relates to a prosthetic fingertip device and, in particular, finger tips associated with prosthetic hands.

BACKGROUND OF THE INVENTION

Modern dynamic upper limb prosthetic terminal devices tend to either be functional or cosmetic, with most common designs making compromises between both aspects. Prosthetic hooks and grippers are particularly good at grasping a variety of objects but are not cosmetic. Conventional electric hands are more cosmetic, but do not allow for conformal grasp or multiple grasp patterns and have difficulty grasping small objects. Multi-articulating hands are also cosmetic, can conform to larger objects that are grasped, and offer multiple grasp patterns. However, multi-articulating hands still have difficulty grasping and manipulating smaller objects. As no single terminal device meets all of the criteria of an ideal terminal device, users often have to physically remove and don different terminal devices to achieve the variety of tasks that they need to perform in their activities of daily living (ADLs).

Products currently on the market that address dexterity include prosthetic fingers by NakedProsthetics, and multi-articulating hands, claiming precision grasp, such as the i-Limb or Bebionic hand. Also included are terminal devices that do not resemble a human hand, but allow for precision grasping, such as the Ottobock Greifer gripper and Motion Control's Electric Terminal Device (ETD) hook-type electromechanical terminal device.

SUMMARY OF THE INVENTION

The present invention provides a prosthetic finger having a fingertip terminal device to enable fine-motor grasping skills. In accordance with an embodiment of the present invention, the prosthetic finger includes a main body and a terminal gripper at the distal end of the main body. The terminal gripper may have two or more jaws or tongs which can open and close relative to one another thereby accomplishing the gripping and releasing motion.

The main body may include a proximal segment attached to a palm and a distal segment pivotally attached to a distal end of the proximal segment, mimicking a human finger. The main body is said to be flexed when the distal segment is pivoted relative to the proximal segment and/or when the proximal segment is pivoted relative to the palm.

In this embodiment, the prosthetic finger may have a gripping mode and a finger flexion mode. In the gripping mode, the at least two tongs of the terminal gripper is able to move relative to one another while the main body is not able to flex, and in the flexion mode, the main body is able to flex while the at least two tongs of the terminal gripper are not able to open and close relative to one another.

The prosthetic finger may further comprise a mode switch for switching between the flexion mode and the gripping mode.

In one embodiment, the mode switch is a lock for enabling the gripping mode and disabling the flexion mode or enabling the flexion mode and disabling the gripping mode by engaging or disengaging the lock. In one version, the lock is a joint lock which engages or disengages the proximal interphalangeal (PIP) joint. In another version, the lock is a sliding lock which engages or disengages at least one of the tongs.

In one embodiment, one of the at least two tongs is stationary and the other one of the at least two tongs is configured to pivot relative to the stationary tong providing the open and close gripper.

In another embodiment, all of the tongs may be movable to cause the gripper to open and close.

The prosthetic finger may further comprise an actuation mechanism for driving the terminal gripper.

In one embodiment, the actuation mechanism includes an interconnect element. The interconnect element could be a cable, chain, link or other interconnect. The actuation mechanism is operable by applying and releasing tension to the interconnect element, which drives the tongs to open and close. The actuation mechanism may be body-powered or electrically-powered.

The tongs may be made from or covered with a textured material preventing slipping.

In another embodiment, the actuation mechanism includes a linkage, a central rack and two pinions, and the tongs are part of the linkage and actuated by the central rack and the two pinions.

In another embodiment, the actuation mechanism may be a wire claw including at least three pre-bent wires. The wire claw may be actuated by a cable and a compression spring.

In another embodiment, the tongs each include a head and a tapering leg, further comprising a block slidably coupled with the legs such that the tongs open or close when the block slides along the legs.

Embodiments of the present invention improve upon hook and hand technology by adding functional dexterity to the aesthetic appeal of multi-articulating hands. The terminal device of the present invention would allow amputees more utility from their prosthesis in tasks requiring fine grasping with two hands, such as tying shoes, or in work activities, such as manufacturing small components. All users would be able to have the best aspects of fine-motor control, the existing gross function, and cosmetic appeal in a single terminal device.

In addition to standard gross-motor control provided by most upper-limb prosthetic terminal devices, this technology enables fine-motor skills with a conformal grasp and the cosmetic appearance of multi-articulating hands.

Artificial limbs are typically grouped as cosmetic, body-powered, and myoelectric. The present device may be applied to bionic devices, such as myoelectric prostheses, which provide electronically powered functionality, such as gripping or releasing, triggered by muscular contractions within the residual limb. The present invention can work in either voluntary-open or voluntary-close modes. It may also be applied to mechanical, body-powered prostheses.

BRIEF DESCRIPTION OF THE INVENTION

DETAILED DESCRIPTION OF THE INVENTION

Figure 1:
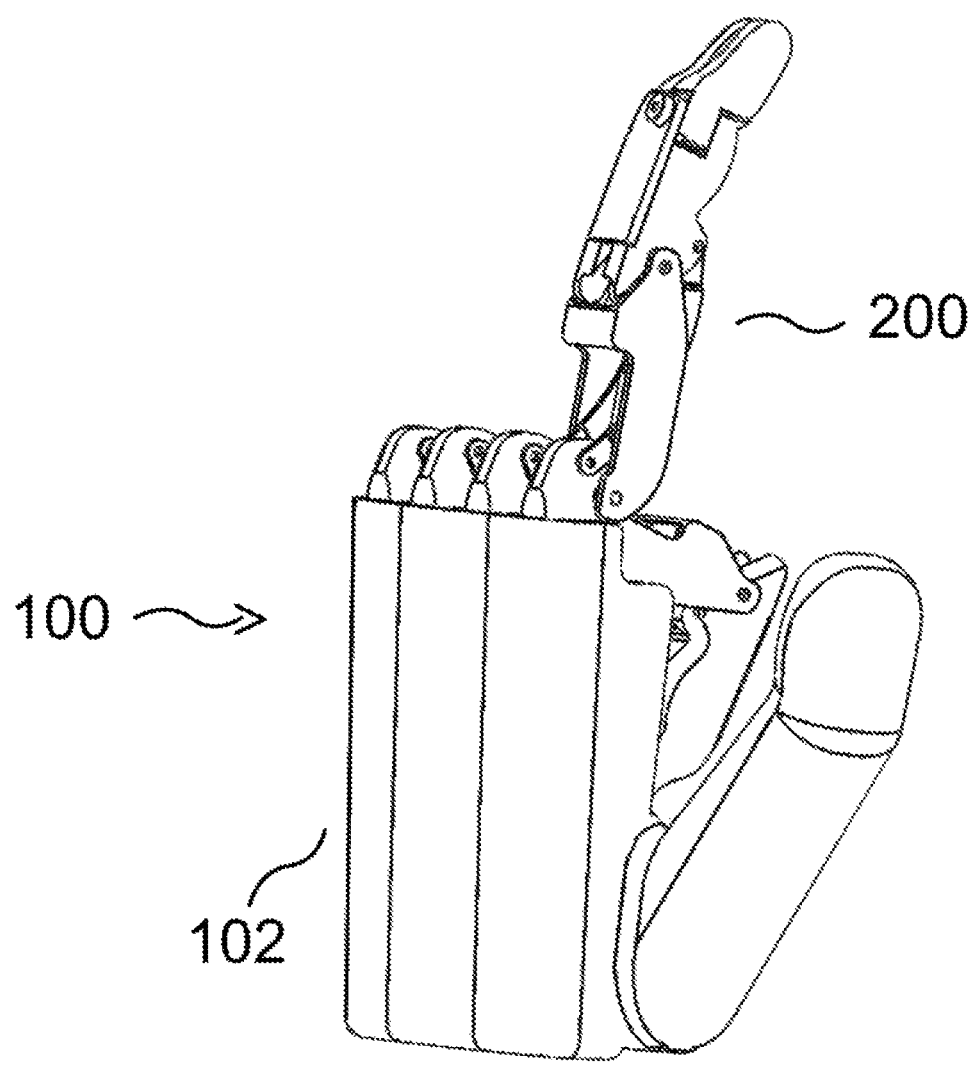
FIG. 1 is a perspective view of a prosthetic hand integrated with a pointer-finger terminal device in accordance with an embodiment of the present invention.
Figure 2:
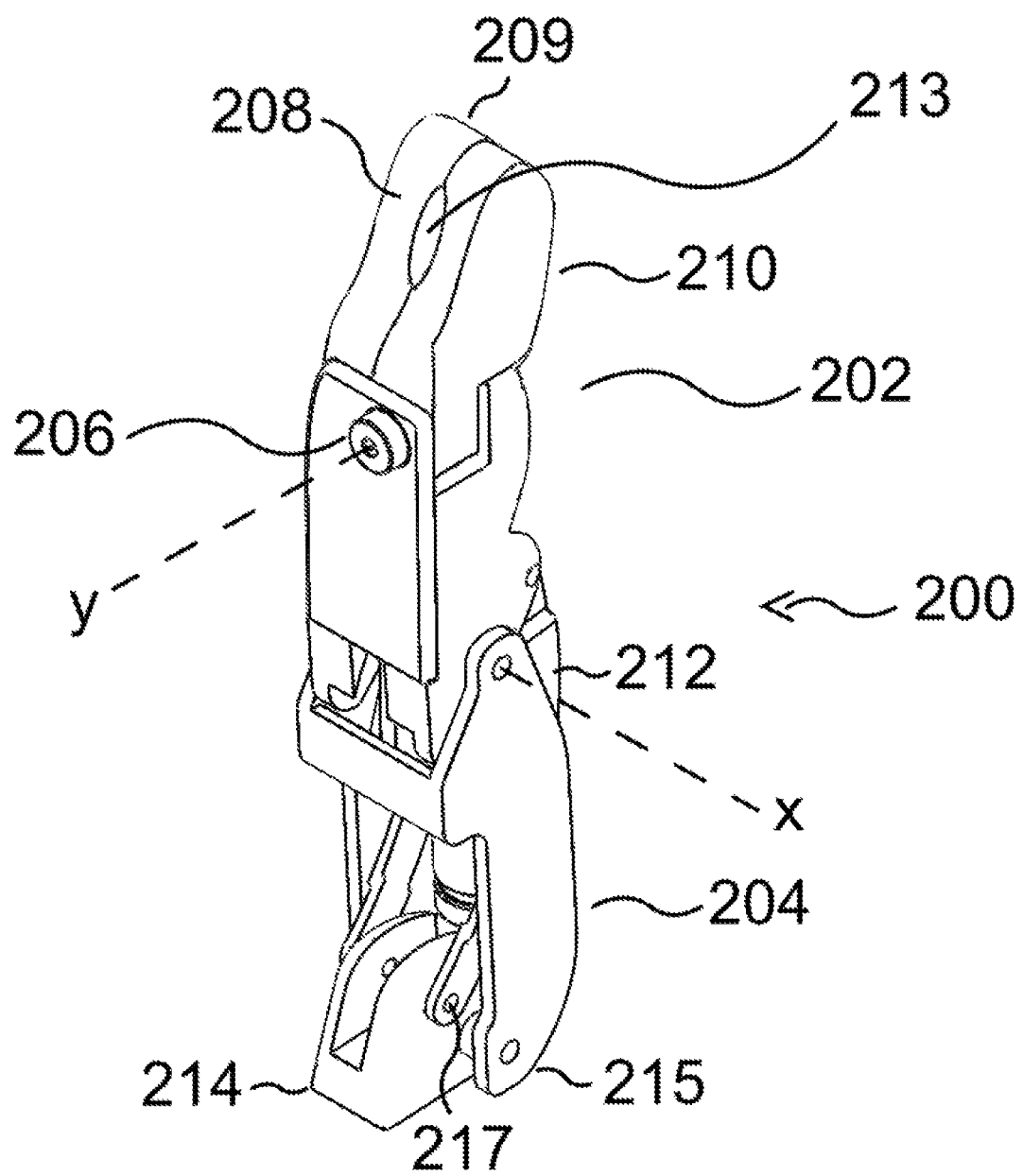
FIG. 2 is a perspective view of the pointer-finger terminal device of FIG. 1 in a closed position.
Figure 3:
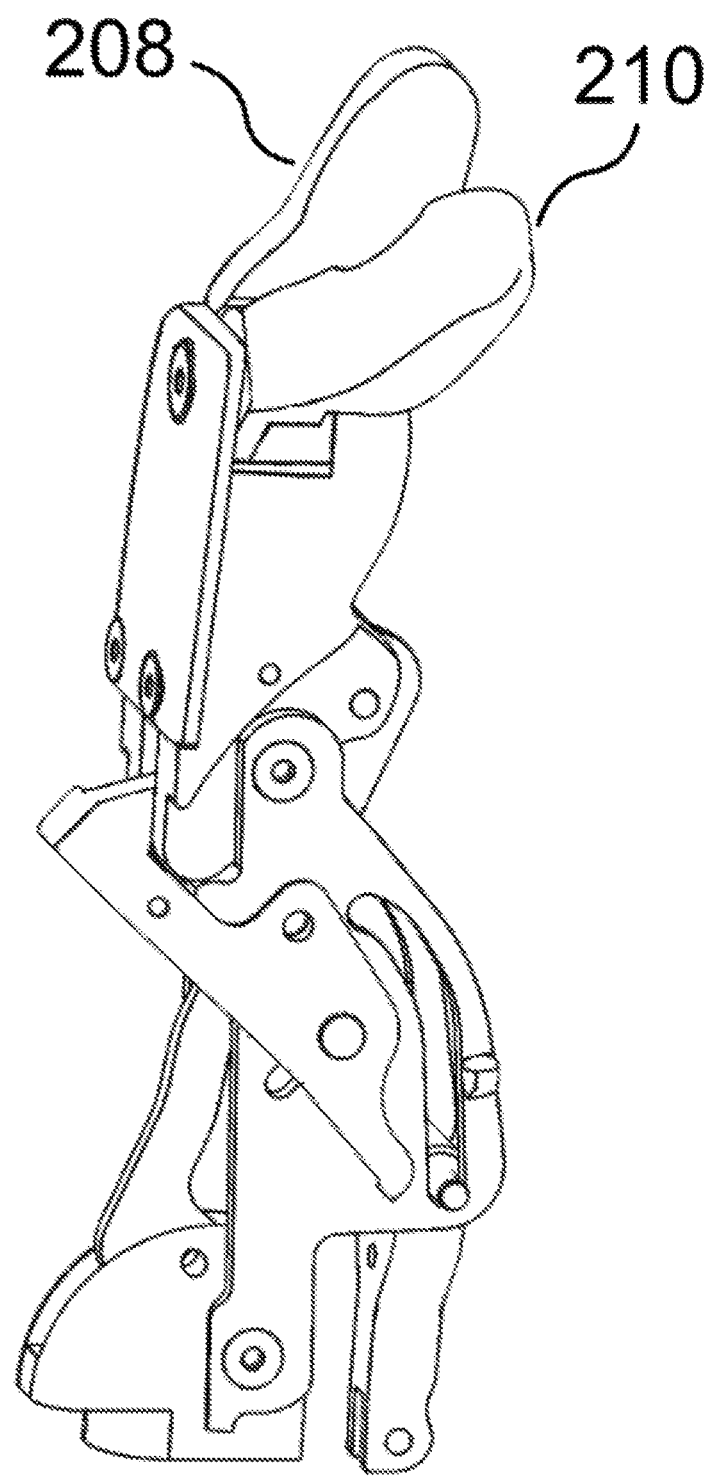
FIG. 3 is a perspective view of the pointer-finger terminal device of FIG. 2 in an open position.

FIGS. 1-3 show an embodiment of the prosthetic finger in accordance with the present invention. Referring to FIGS. 1 and 2, a prosthetic hand 100 integrated with a pointer-finger 200 of FIG. 2 is schematically depicted in FIG. 1. Other fingers of the prosthetic hand are flexed and not shown.

Referring to FIG. 2, in this embodiment, the finger 200 may include a proximal segment 204 and a distal segment 202. The distal segment 202 may be attached to a distal end of the proximal segment 204 at a pivot joint 212 such that the distal segment can rotate about the joint 212 about an axis x relative to the proximal segment 204 mimicking finger flexion. At a proximal end 215 of the proximal segment 204, a connecting piece 214 is used to connect the finger 200 to a palm 102, as shown in FIG. 1. The connecting piece 214 is connected to the proximal segment at a pivot point 217. The distal segment 202 may include two jaws 208 and 210. One jaw 208 may be stationary. The other jaw 210 is attached at a pivot joint 206 such that the jaw 210 may pivot about the joint 206 about an axis y relative to the stationary jaw 208. The shape of the two jaws 208, 210 may be flat on the inside surface such that the two jaws are flush with each other or notched on the inside surface such that when two jaws meet, there is a notch 213. The notch 213 is helpful to keep the objects from slipping away from the gripper. The pivot point 206 may be oriented such that the axis y is perpendicular to the axis x. The pivot point 206 may also be oriented with the axes x and y at other relative angles, though being perpendicular may be preferred. In FIGS. 1 and 2, the jaw 210 is shown to be in a closed position. In FIG. 3, the jaw 210 is in an open position.

Figure 4:
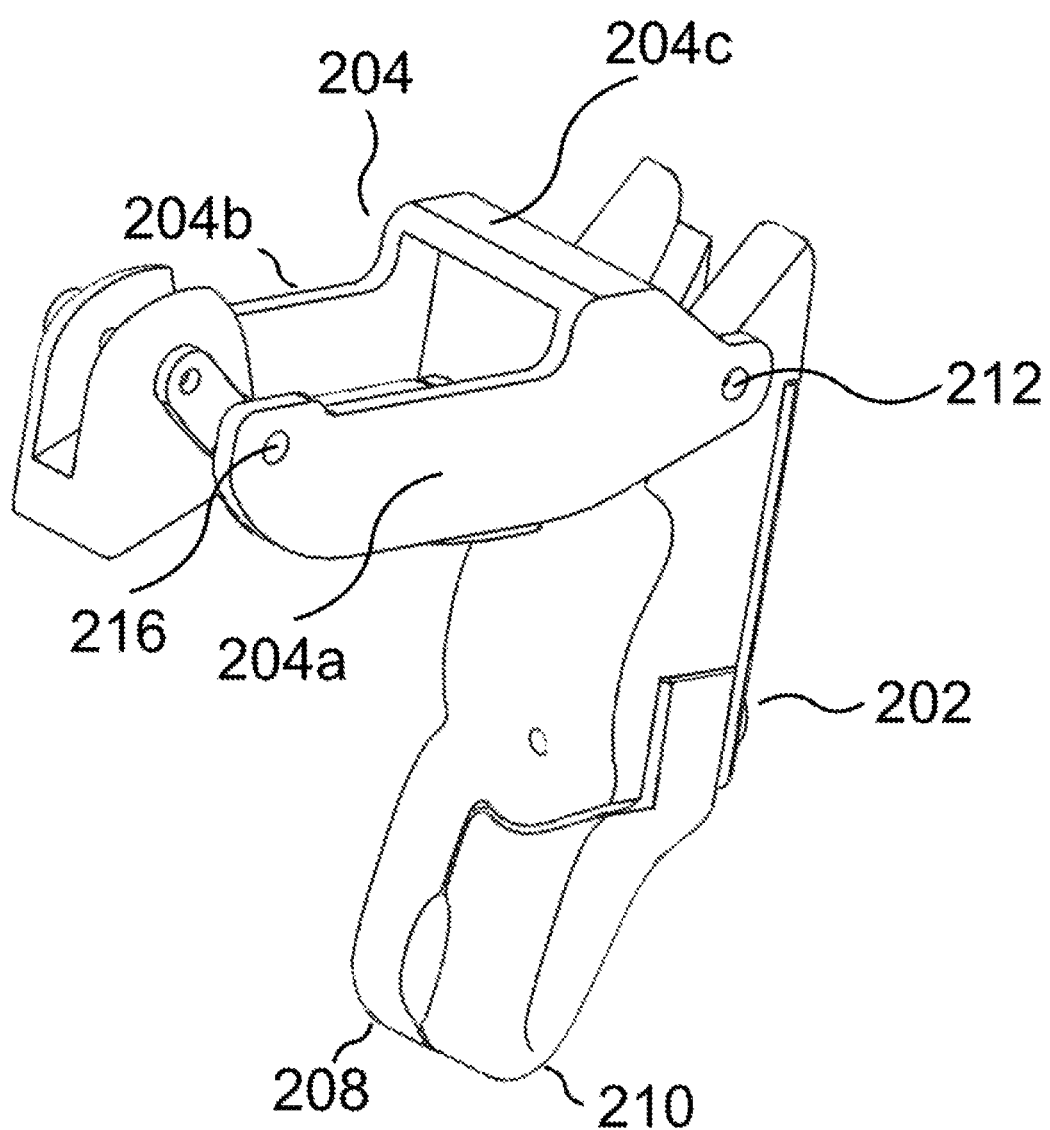
FIG. 4 is a perspective view of a part of the pointer-finger terminal device of FIG. 2 in a flexed position.

In this embodiment, the proximal segment 204, more clearly shown in FIG. 4, includes two parallel side plates 204a, 204b connected by a middle portion 204c. The two side plates 204a, 204b and the middle portion 204c form a housing for placing the actuation mechanism and a part of the connecting piece 214.

Referring back to FIG. 2, the proximal segment 204, the stationary jaw 208 and the movable jaw 210 mimic the three segments of a finger digit. In this embodiment, the joint 206 is located around the middle of the stationary jaw 208. The movable jaw 210 is about half the length of the stationary jaw 208. In another embodiment, the pivot point 206 may be located anywhere between the tip 209 of the finger 200 and the pivot point 212. In FIG. 4, showing the flexion mode, the proximal segment 204 is rotated relative to the distal segment 202 about the proximal interphalangeal (PIP) joint and relative to the palm of the hand about the metacarpophalangeal (MCP) joint such that the finger 200 is shown to be in a bent position, mimicking flexion of a finger digit. In this embodiment, the distal interphalangeal (DIP) joint is fixed in the flexion mode.

In general, the prosthetic finger shown in FIGS. 1-3 includes two modes, namely a finger flexion mode and a gripping mode. In the finger flexion mode, the finger is operable to flex but the jaws at the fingertip are constrained to not open or close. In the gripping mode, the jaws are operable to open and close but the finger is constrained from flexing. The transition between two modes may be achieved by a mode switch operation.

In one embodiment, the mode switch may include a joint lock 218, as illustrated in FIGS. 5-9. The joint lock 218 is a piece having two parallel sides 218a, 218b connected by a middle portion 220. The two sides 218a, 218b and the middle portion 220 form a gap. Each side plate 218a, 218b may have a protrusion 219a, 219b respectively. At the middle portion 220, there is a protrusion 222. The protrusions 219a, 219b and the protrusion 222 form a recess 226 on each side plate. The proximal segment 204 of the dexterous fingertip is placed between the gap of the joint lock 218 and oriented such that the sides 218a, 218b are parallel to the side plates 204a, 204b. The proximal segment 204 is pivotally attached to the joint lock 218 at a pivot point 228 on each side. The protrusion 222, along with the recess 226, is shaped to catch on the distal segment 202, thereby locking the PIP joint 212. Each side plate 218a, 218b may further have a narrower end portion 224, which is configured to engage an upper end 245 of a linkage 250. On each side plate 204a, 204b of the proximal segment 204, there is an elongated slot 230 having an upper end 232 and a lower end 234. The upper end 245 of the linkage 250 slides along the slot 230 and is used as a stroke limiter, which will be described herein below.

Figure 5:
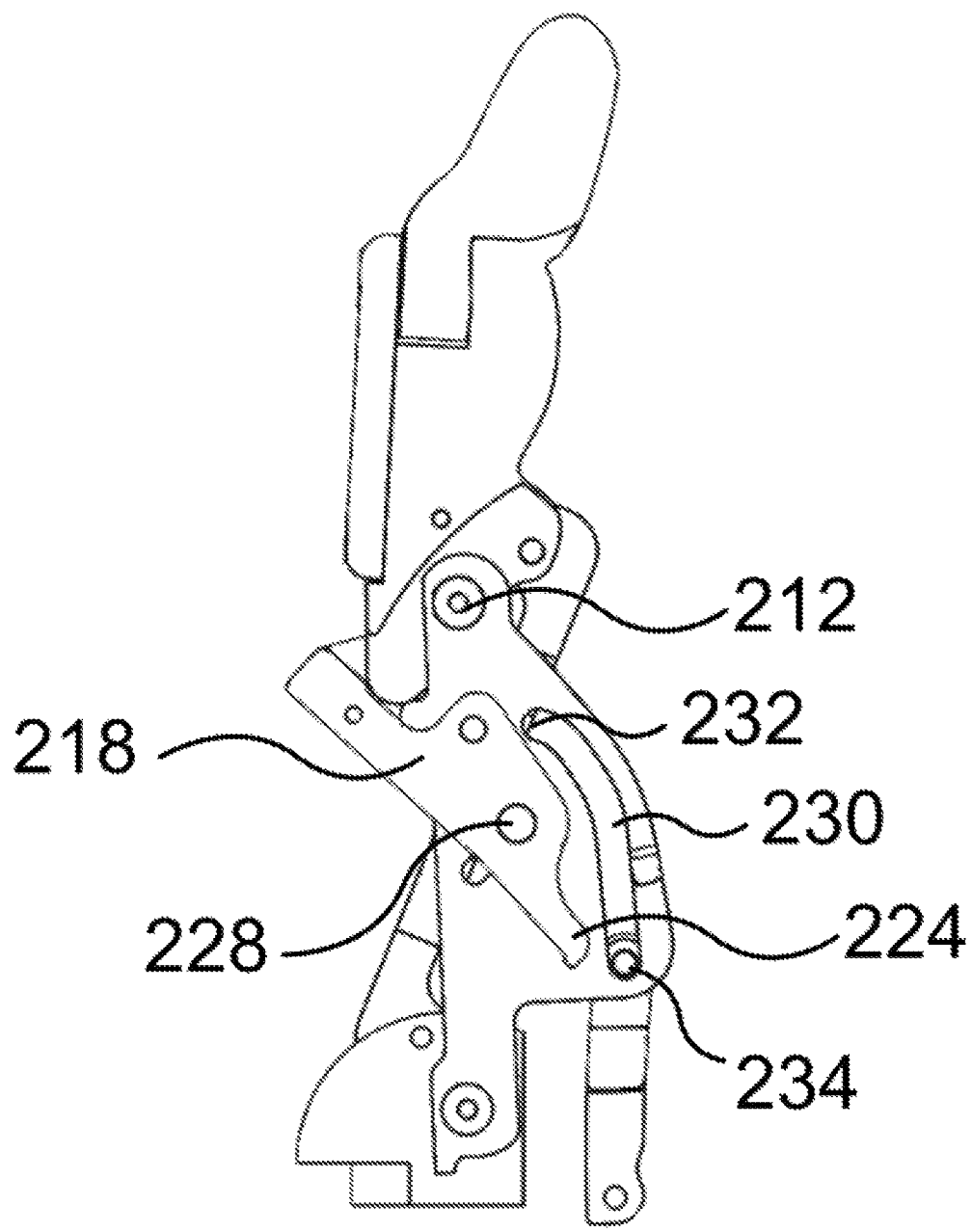
FIG. 5 is a side view of the pointer-finger terminal device of FIG. 2 in a close position.
Figure 7:
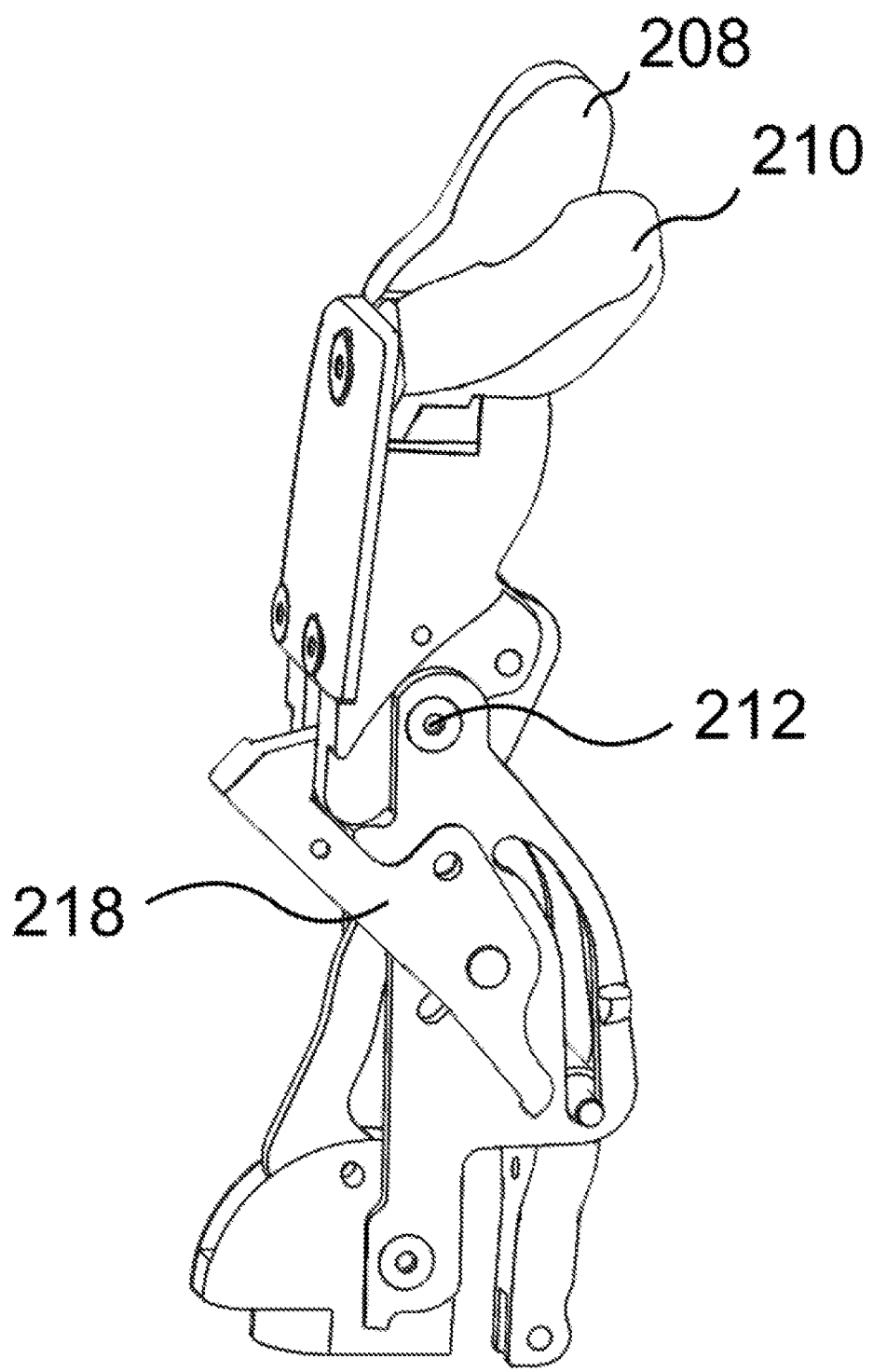
FIG. 7 is a perspective view of the pointer-finger terminal device of FIG. 2 in a grasping mode in an open position.
Figure 8:
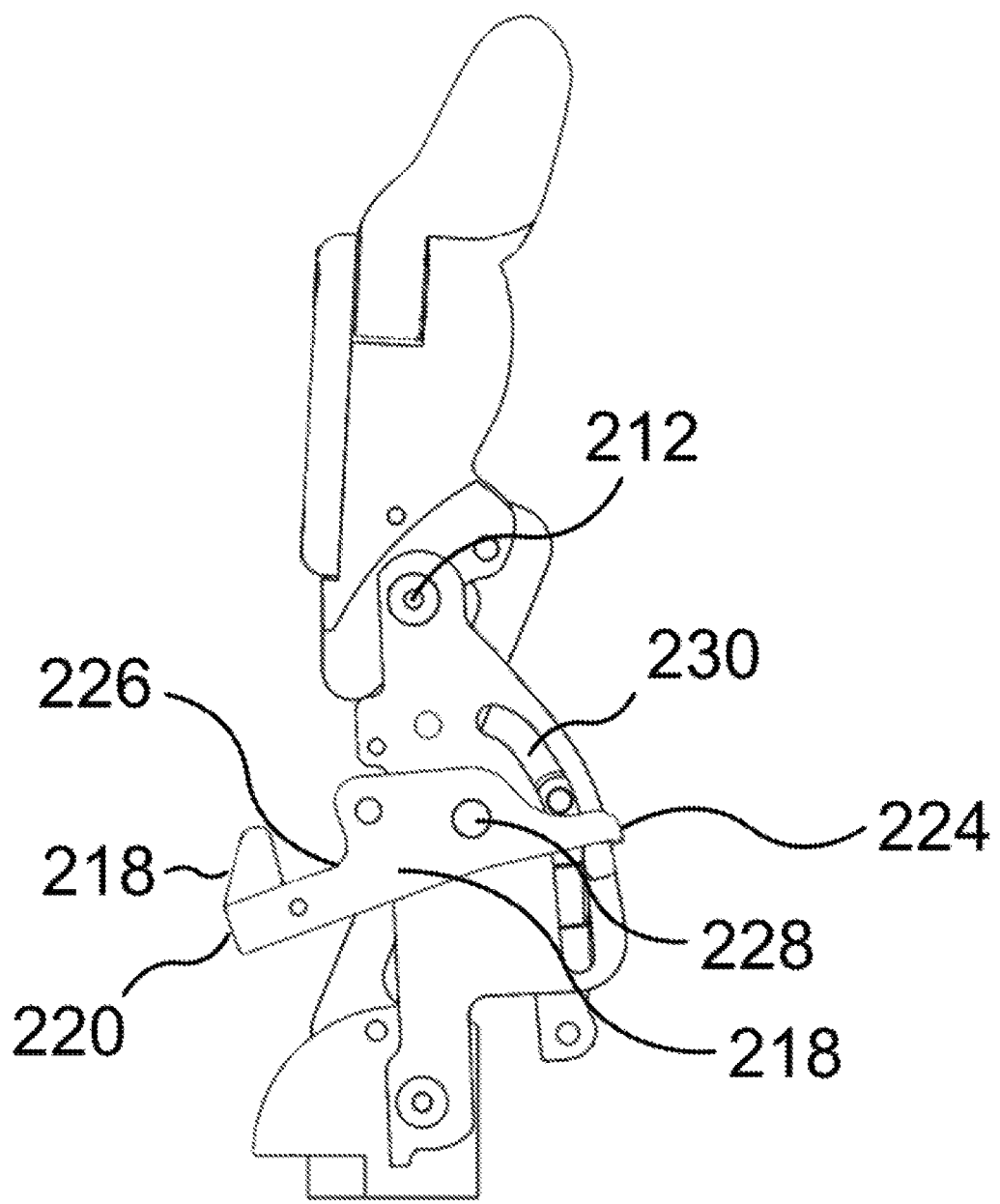
FIG. 8 is a side view of the pointer-finger terminal device of FIG. 2 in the flexion mode in an unflexed position.
Figure 9:
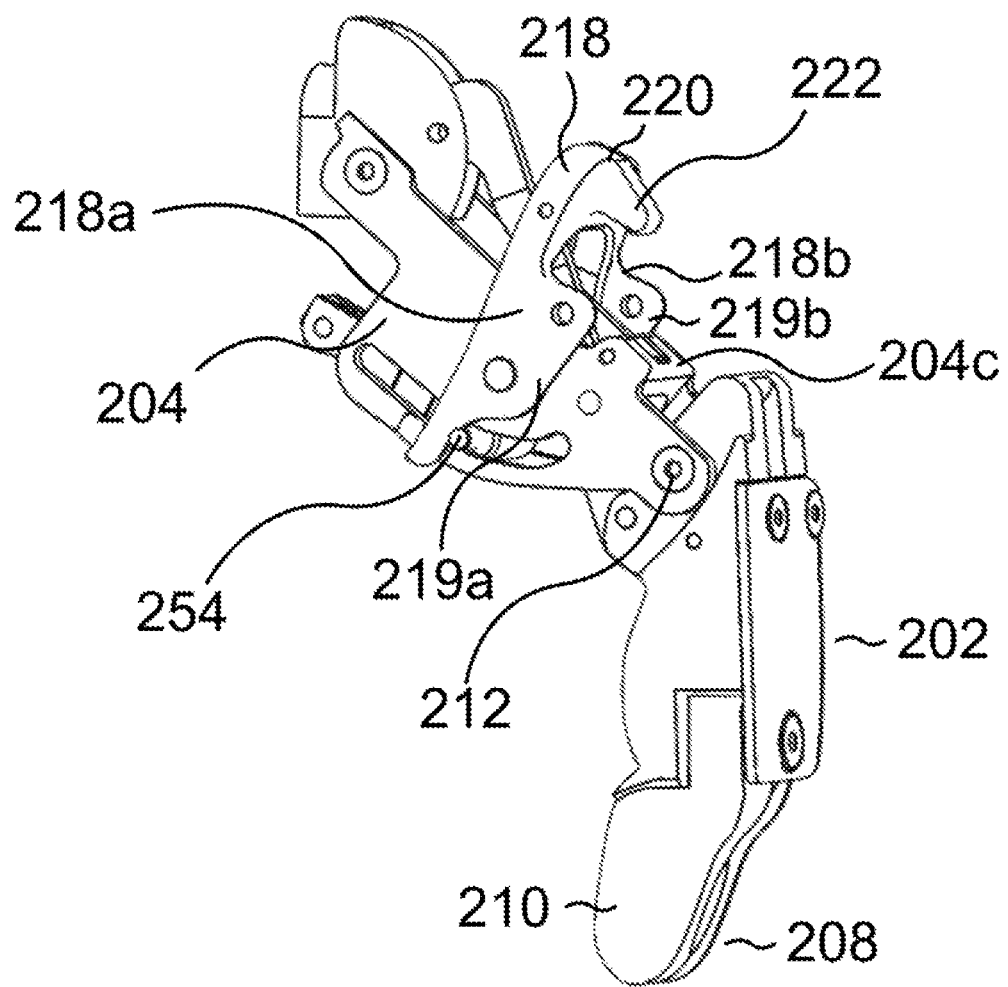
FIG. 9 is a perspective view of the pointer-finger terminal device of FIG. 2 in the flexion mode in a flexed position.

An interconnect element (not shown) such as a cable, chain or linkage, may be connected to a lower end 252 of the linkage 250. For example, a cable interconnect is tensioned to begin opening the gripper when the stroke limiter 245 passes the narrower end portion 224 of the joint lock 218, as shown in FIGS. 5 and 7, when the lock 218 is in a locked position. When the joint lock 218 is in an unlocked position, as shown in FIGS. 8 and 9, when the cable interconnect is tensioned, the stroke limiter 245 is stopped by the narrower end portion 224 of the joint lock 218 therefore doesn't travel fully to the lower end of the slot 230. As such, there is not enough tension to cause the gripper to open. In the meantime, since the joint lock 218 is unlocked freeing the PIP joint, pulling on the cable interconnect will cause the finger to flex.

Figure 10:
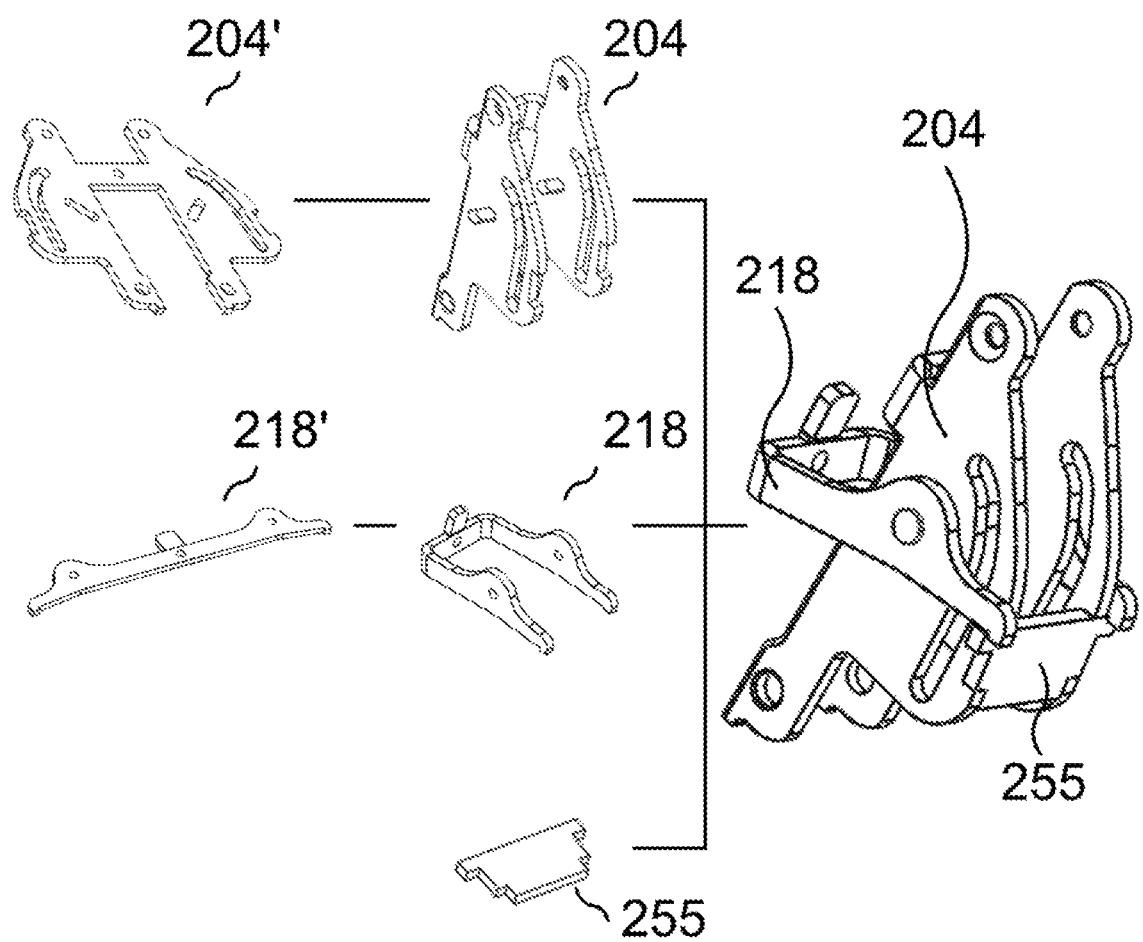
FIG. 10 is a perspective view of a planar assembly for a part of the pointer-finger terminal device of FIG. 2.

The proximal segment 204 of the fingertip and the joint lock 218 can be built from planar pieces of material that are then folded into the correct shape. Sub-assemblies can be folded and built into the full assembly, as shown in FIG. 10. The proximal segment 204 can be made by folding a planar part 204'. The lock 218 can be made by folding a planar part 218'. A piece 255 is included to keep the assembly in place.

Figure 6:
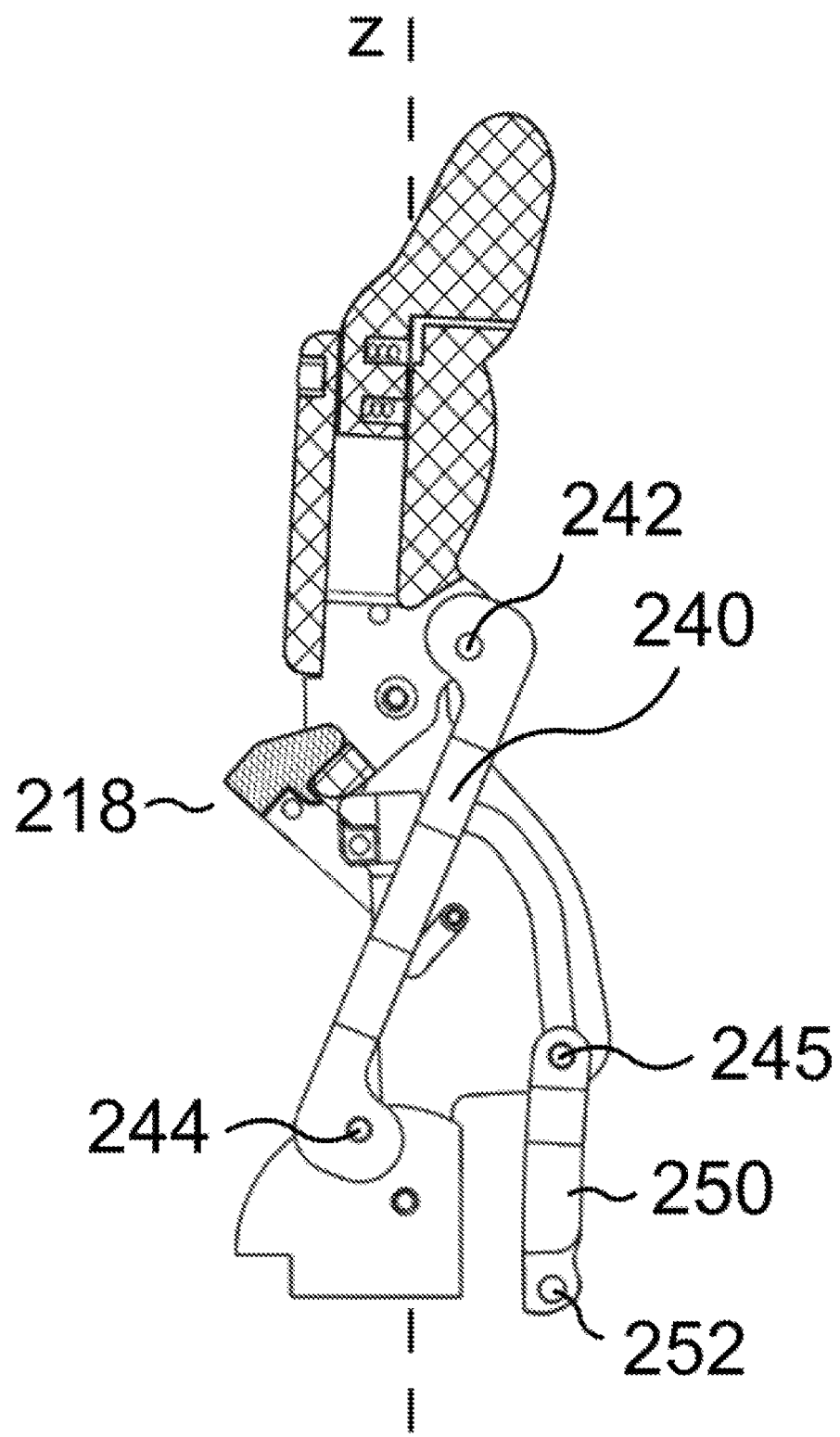
FIG. 6 is a cross-sectional side view of the pointer-finger terminal device of FIG. 2.

In FIG. 6, which provides a cross-sectional side view of the prosthetic finger, a lever arm element 240 can be seen. In this example, the lever arm element 240 is connected to the distal segment 202 at one end 242 and connected to the connecting element 214 at the other end 244. The lever arm 240 allows the finger to flex relative to the palm. In the gripping mode, flexion is prevented by engaging the joint lock 218 into the PIP joint 212, effectively locking the joint. In the finger flexion mode, the joint lock 218 is disengaged from the PIP joint. The joint lock is operable by one hand and is stable in both modes. The actuation for the lock may be integrated with the hand.

Figure 11:
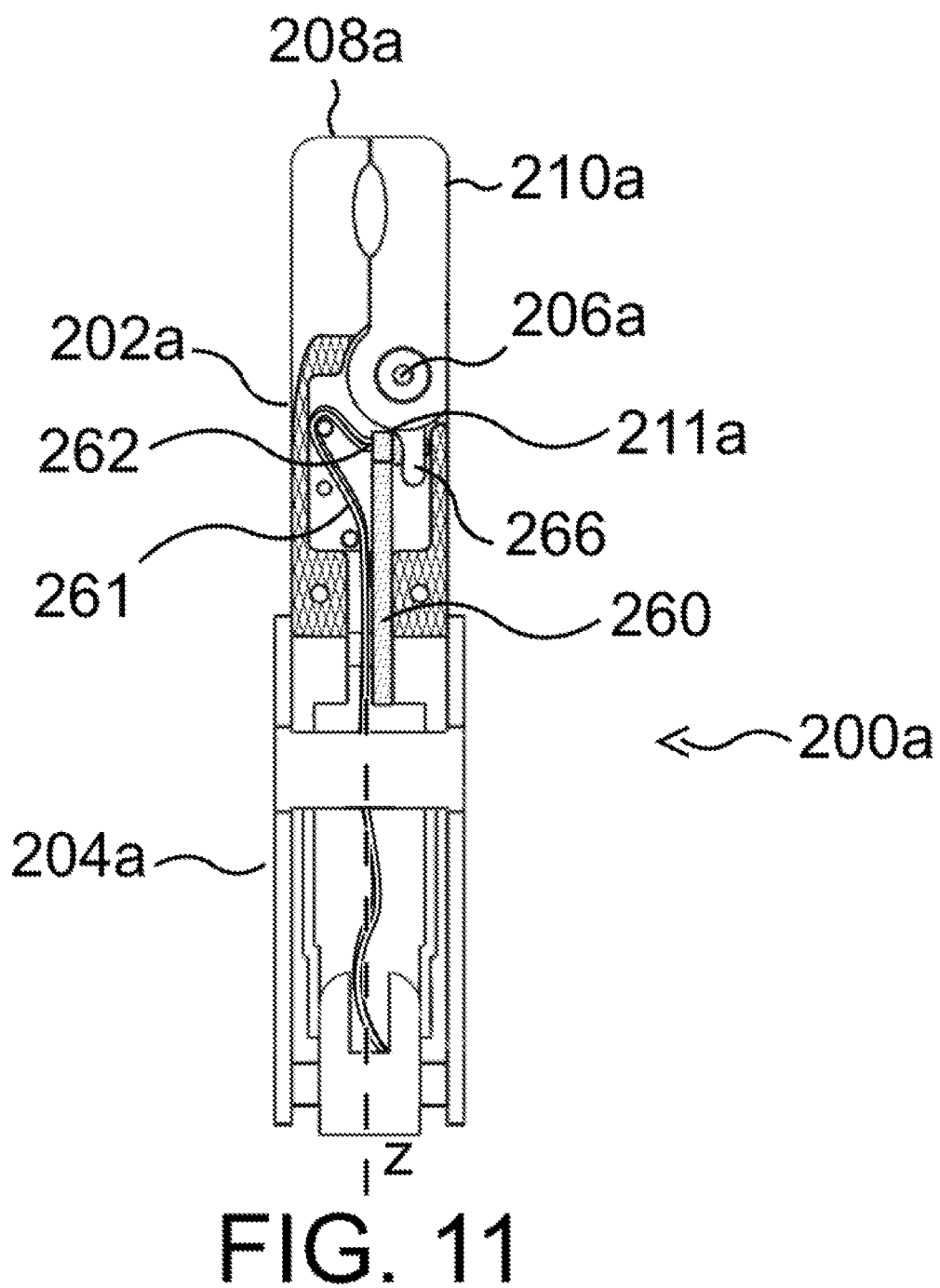
FIG. 11 is a top view of a pointer-finger terminal device having a sliding top-lock in a flexion mode.
Figure 12:
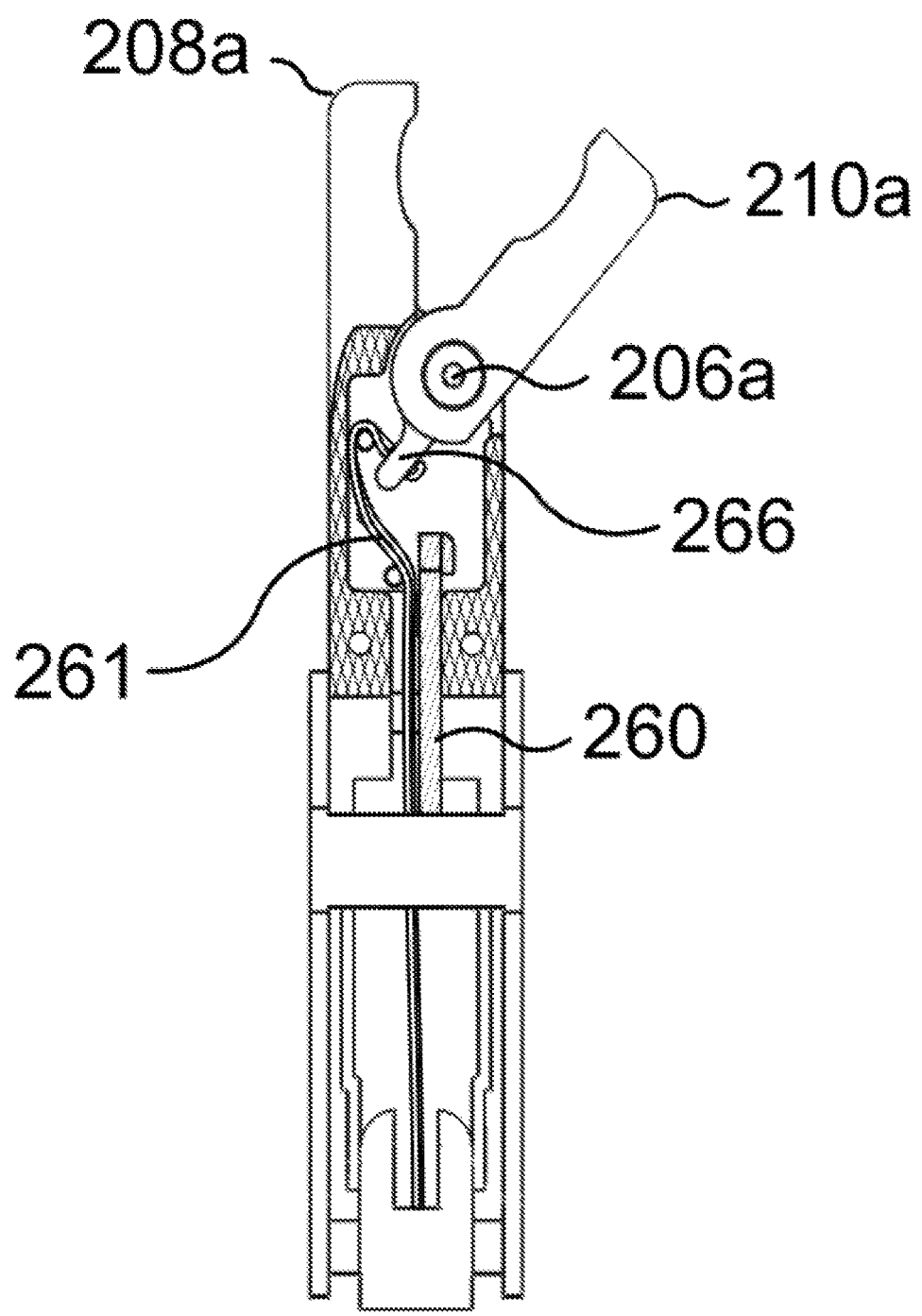
FIG. 12 is a top view of the pointer-finger terminal device having a sliding top-lock showing the finger terminal device in a grasping mode.

In another embodiment, as shown in FIGS. 11 and 12, the mode switch is a sliding lock 260 on the dorsal side of the fingertip. In this example, the prosthetic finger 200a is similar to the prosthetic finger 200. The finger 200a includes a distal segment 202a and a proximal segment 204a. In this embodiment, the sliding lock 260 takes the form of a straight long bar oriented at a direction parallel to a z-axis of the prosthetic finger 200a. The distal segment 202a of the finger 200a includes a stationary jaw 208a and a movable jaw 210a. The movable jaw 210a is attached to the stationary jaw 208a at a pivot joint 206a such that the jaw 204 may pivot about the joint 206 relative to the stationary jaw 208. In FIG. 11, the jaw 210a is shown to be in a closed position.

Figure 12B:
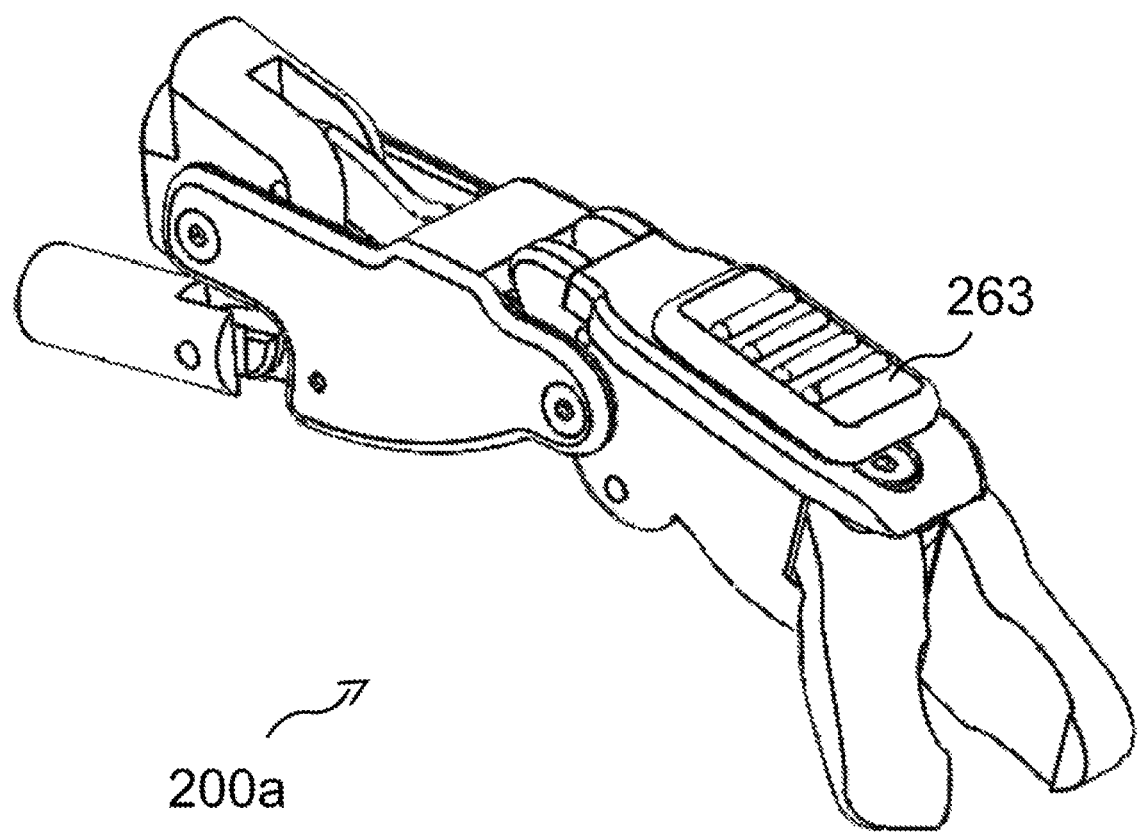
FIG. 12B is a perspective view of the pointer-finger terminal device having a sliding top-lock showing the finger terminal device in a grasping mode.

At the distal end 211a of the movable jaw 210a, there is a protrusion 266 to be used as a jaw stop and a connection point for a tensioning interconnect, such as a cable 261, as shown in FIGS. 11 and 12. The cable 261 attached at the connection point 266 to act as a lever for the moving jaw 210a. In the finger flexion mode, the sliding lock 260 is moved distally along the z-axis engaging the jaw stop 266 as shown in FIG. 11, the tension pulls on the whole finger and flexes the finger. In gripping mode, the sliding lock is moved proximally disengaging the stop 266 thereby locking the PIP joint preventing finger flexion. The same interconnect then opens the gripper, as shown in FIG. 12. FIG. 12B is a perspective view of the exterior appearance of the terminal device embodied in FIGS. 11 and 12. A sliding switch 263 is provided to be connected with the sliding lock 260. Pushing the switch 263 up and down will cause the sliding lock 260 to move accordingly.

Figure 13:
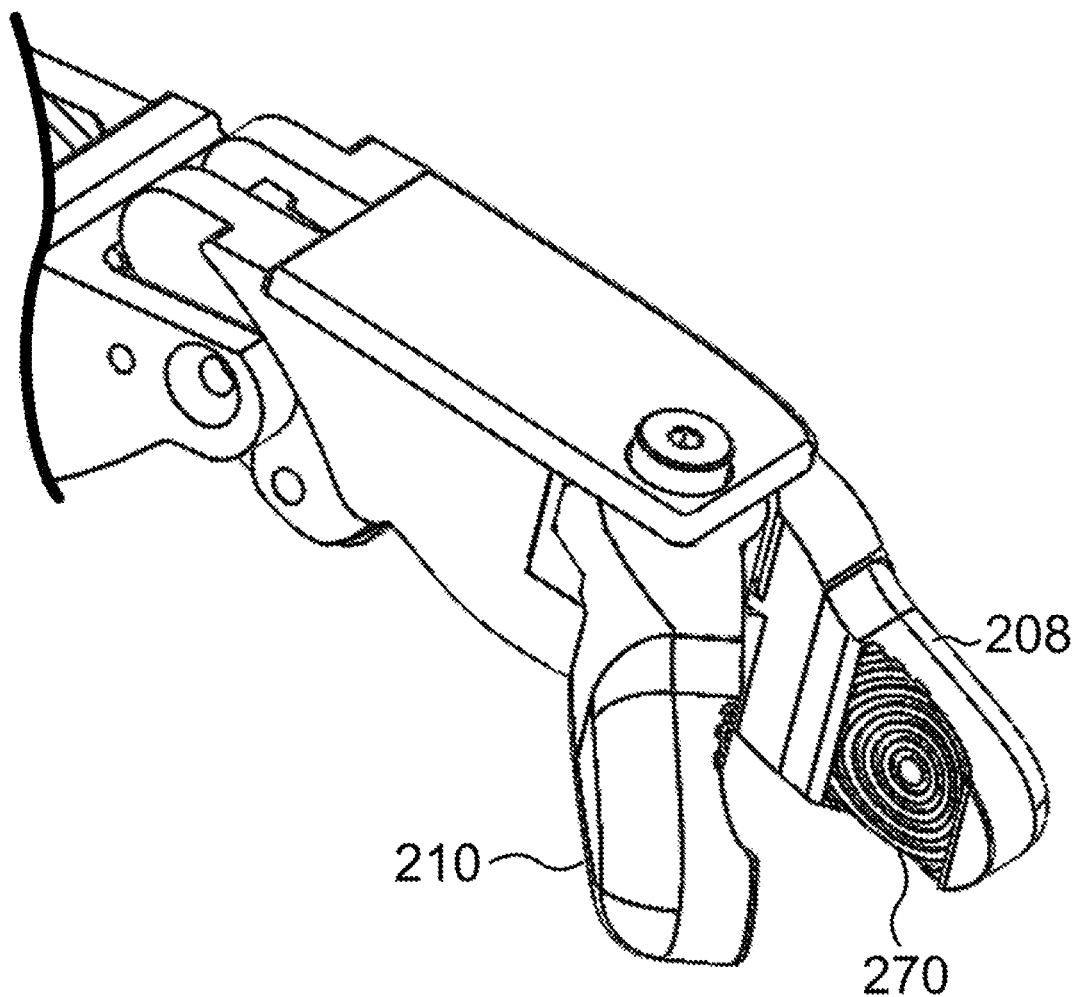
FIG. 13 is a perspective view showing a finger terminal device with tongs having a conformal finger pulp grip surface.
Figure 14:
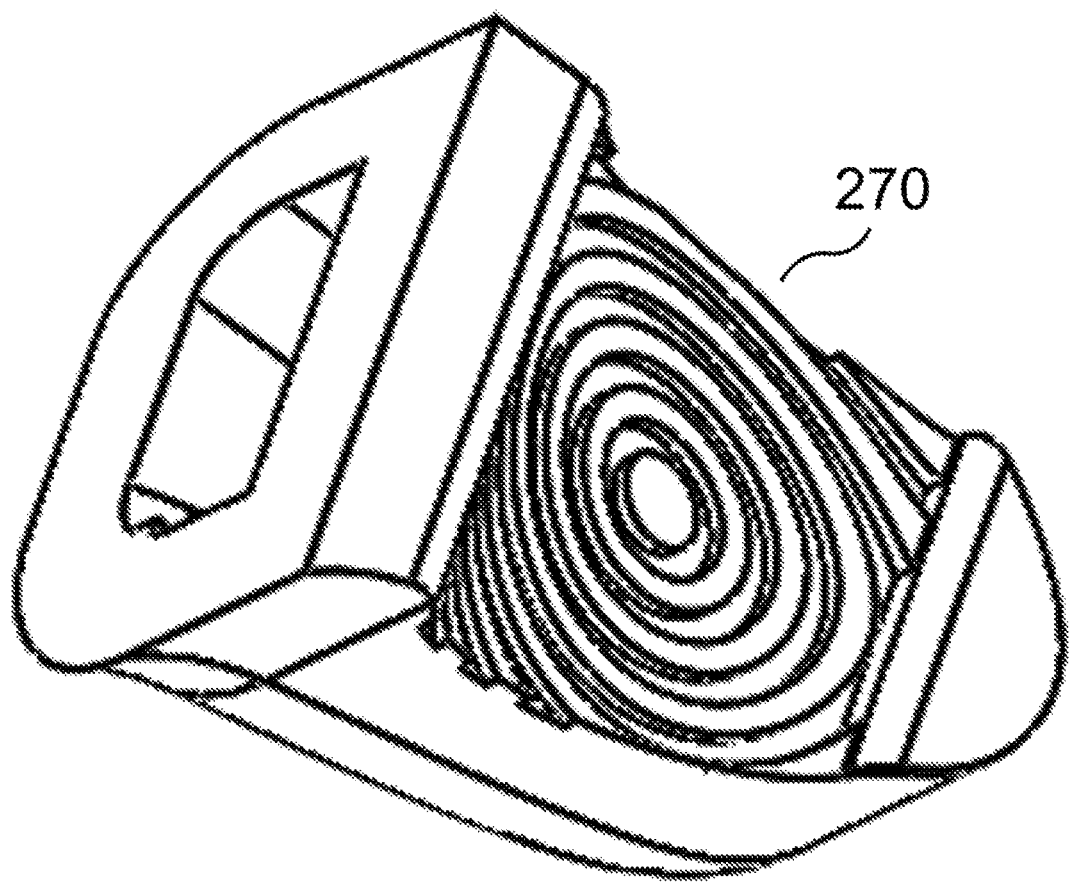
FIG. 14 is an enlarged perspective view of the conformal finger pulp grip surface.

Conformal material 270 may be added to the tip of both the moving and stationary jaws, as shown in FIGS. 13 and 14. The gripping surface wraps fully around the most distal segment in order to provide conformity, additional compliance and friction when bringing the jaws together in the fingertip mode. The surfaces can be texturized to further increase grip friction.

Figure 15:
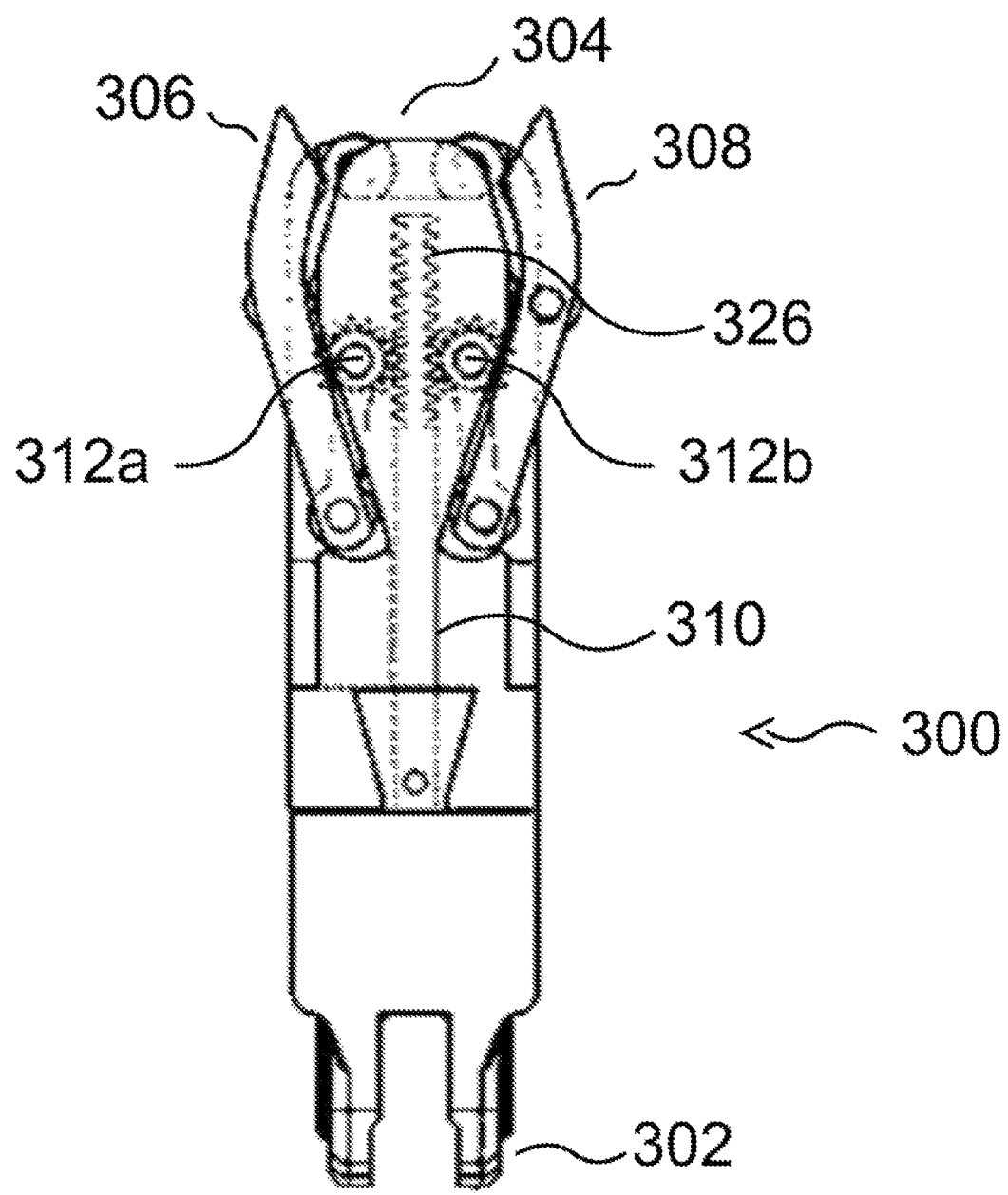
FIG. 15 is a top view of an end effector in accordance with another embodiment in an undeployed position.
Figure 16:
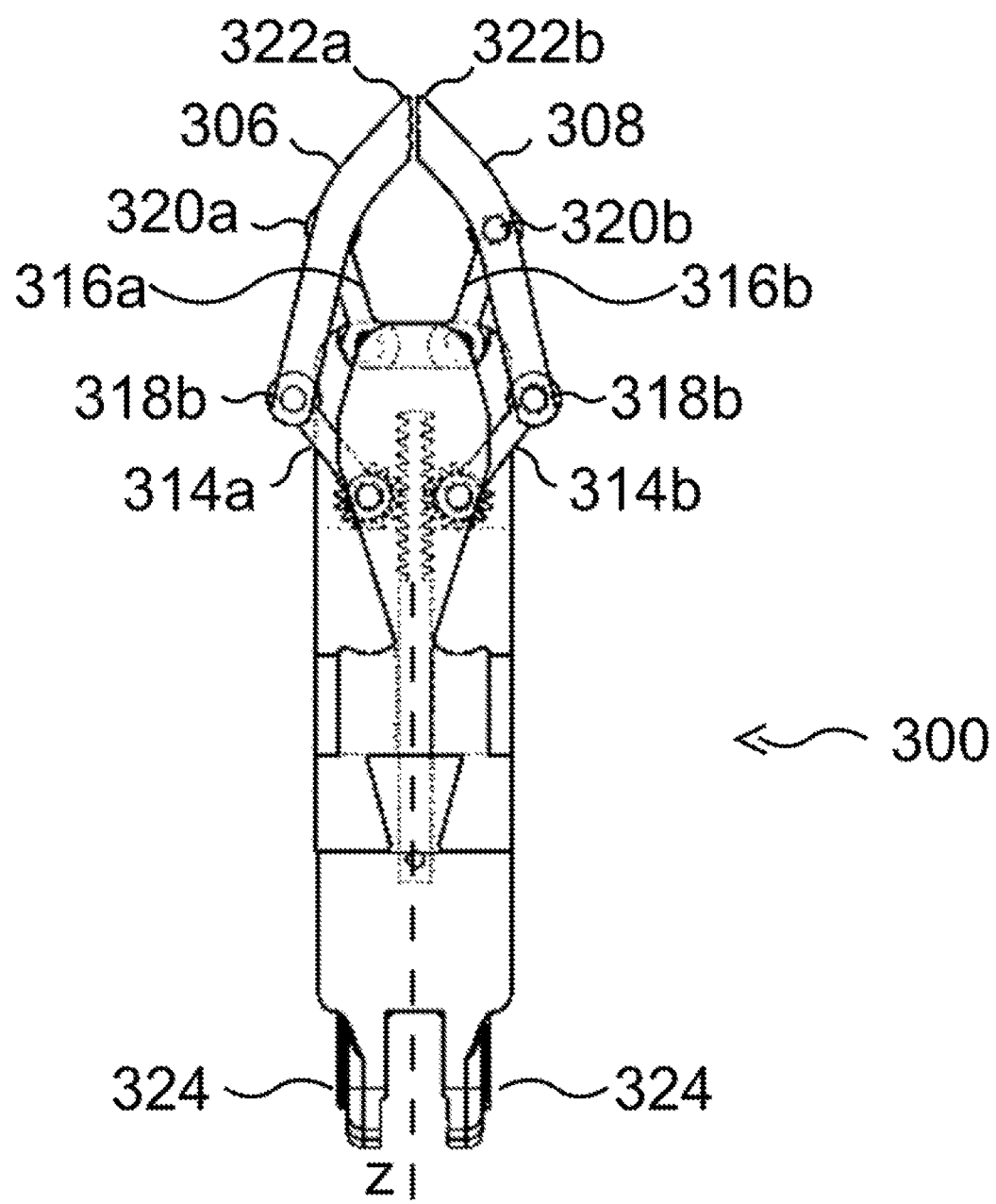
FIG. 16 is a top view of the end effector of FIG. 15 in a deployed position.

The distal segment 202 of the finger 200 may have various embodiments with various configurations. FIGS. 15-16 show a distal segment 300 of a prosthetic finger according to another embodiment, i.e., a rack-pinion extending pincer. In this embodiment, the distal end 304 of the index finger has two arms or jaws 306, 308 that open and extend outward, and when fully extended come together to form the gripper. The arms or jaws 306, 308 are part of a 6-bar linkage and are actuated symmetrically by a central rack 310 and two pinions 312. The rack 310 is a long strip of bar disposed in the center of the distal segment 300 widthwise and along the z-axis of the distal segment. A toothed bar 326 is coupled to the rack and slides. Two pinions, one on each side of the central rack, engage with the toothed bar 326 of the central rack. The two pinions and the central rack 310 are fixedly attached to the distal segment 300. The toothed bar 326 can slide along the central bar up and down. Two bars 314a, 314b each are attached to one of the pinions on one end and, on the other end, attached to a proximal end of one of the arms 306, 308. Another two bars 316a, 316b each are attached to the distal end 304 of the distal segment 300 on one end and, on the other end, attached to the middle portion of one of the arms 306, 308. In FIG. 16, we will refer to the direction towards the distal end as up and the direction towards the proximal end as down. As the pinions engages the teeth of the rack, the teeth of the rack slides down the central rack, rotating one end of the bars 314a, 314b and causing the other end of the bars 314a, 314b to push the arms 306, 308 up. In the meantime, the bars 316a, 316b extend away from the distal end and push the arms 306, 308 up such that the distal end 322a, 322b of the arms 306, 308 join together to form a gripper.

The gripper can be actuated with an additional rigid linkage coupled to the central rack to both extend and retract the arms or jaws. In another embodiment, a cable can be attached to the central rack to apply tension to a cable to extend the arms/jaws. A spring can be used to retract them. The spring may be an extension or compression spring depending on the placement. The spring could be placed inline around the sliding rack. The spring would push or pull against the rack and resist the cable or actuator in tension. In FIG. 16, the arms or jaws 306, 308 are shown to be fully extended to form a gripper. The proximal end 302 of the distal segment 300 is configured to be attached to a proximal segment such as the proximal segment 204 at the pivot point 324.

Figure 17:
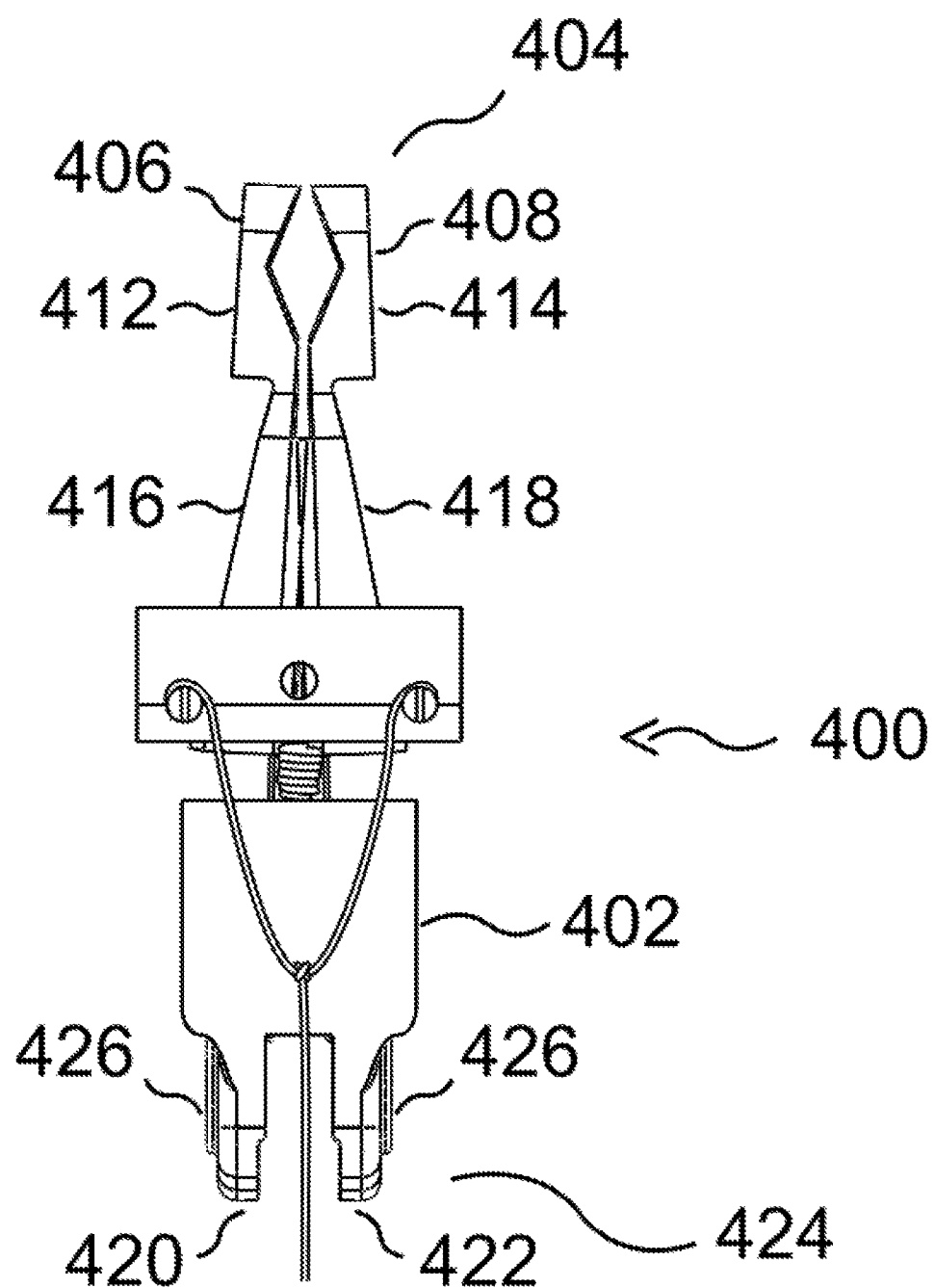
FIG. 17 is a top view of an end effector in accordance with another embodiment in an undeployed position.
Figure 18:
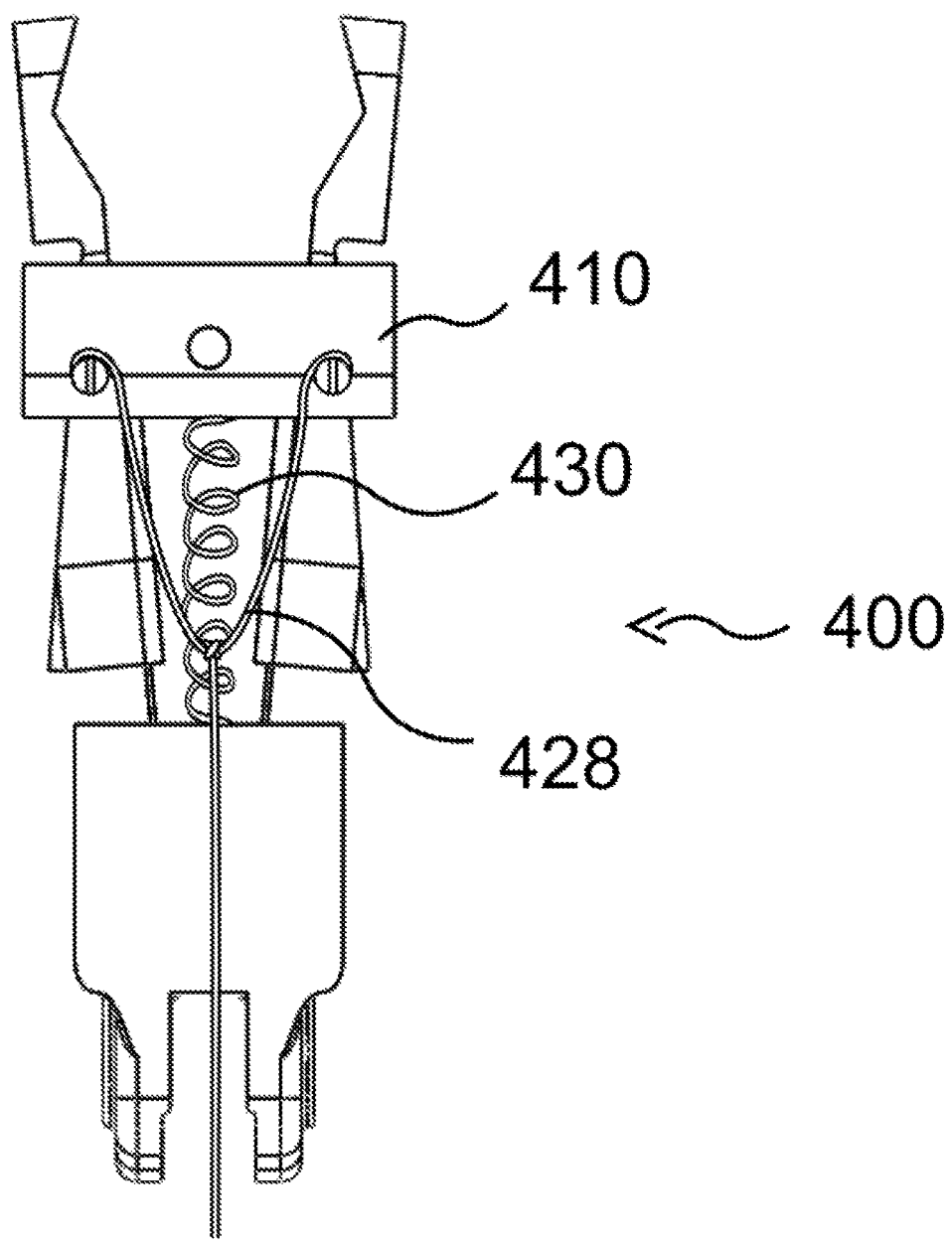
FIG. 18 is a top view of the end effector of FIG. 17 in a deployed position.
Figure 19:
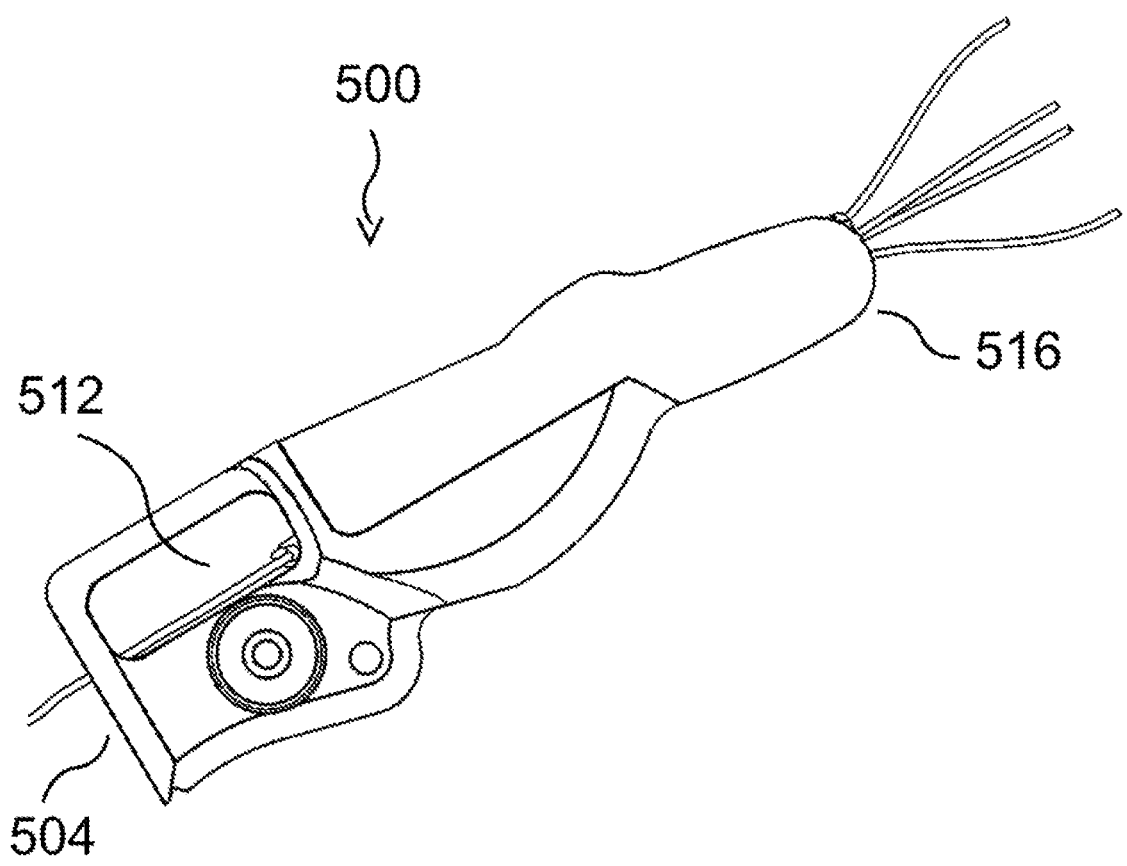
FIG. 19 is a side view of an end effector in accordance with another embodiment in a deployed position.
Figure 20:
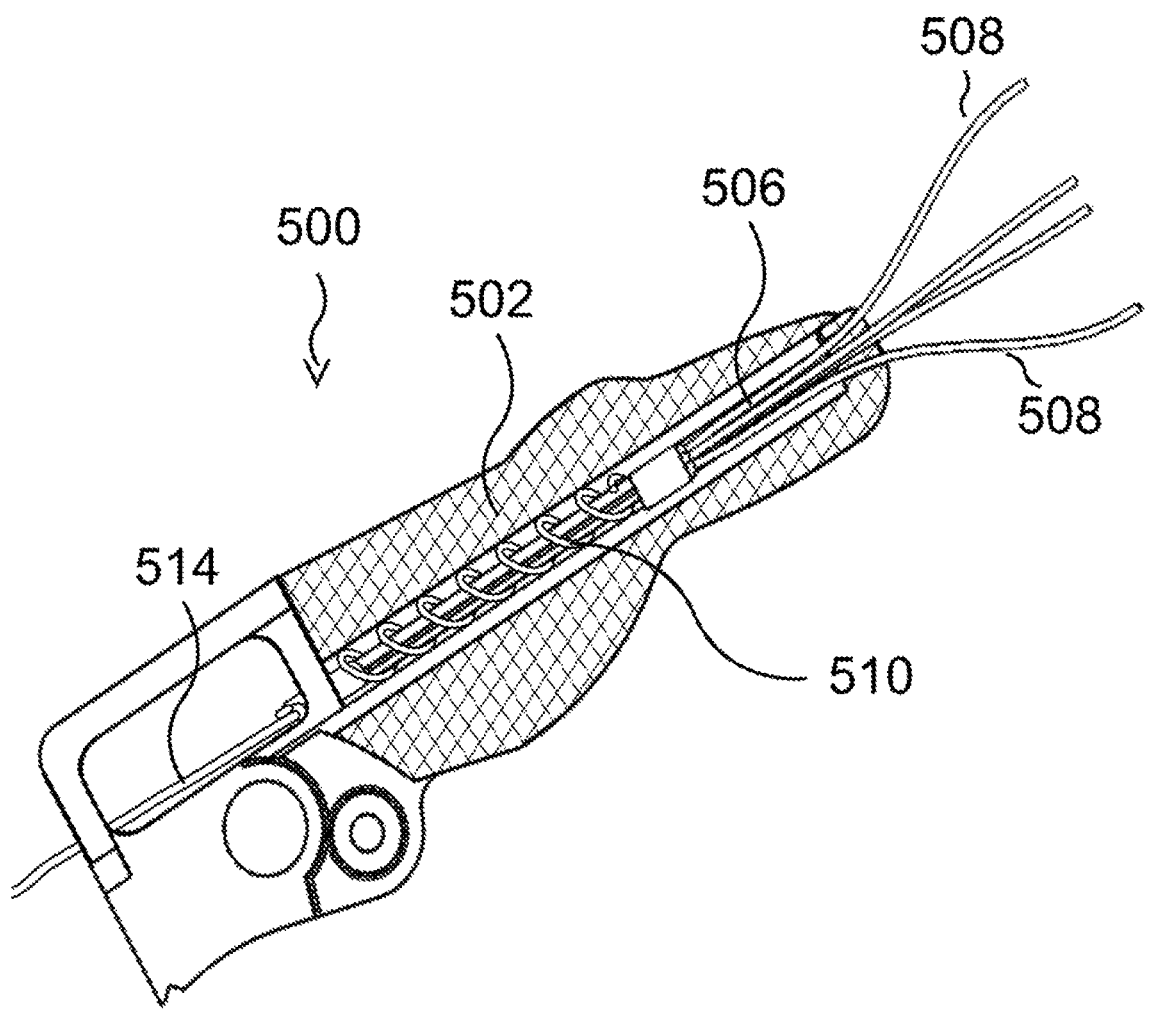
FIG. 20 is a cross sectional side view of the end effector of FIG. 19 in a deployed position.
Figure 21:
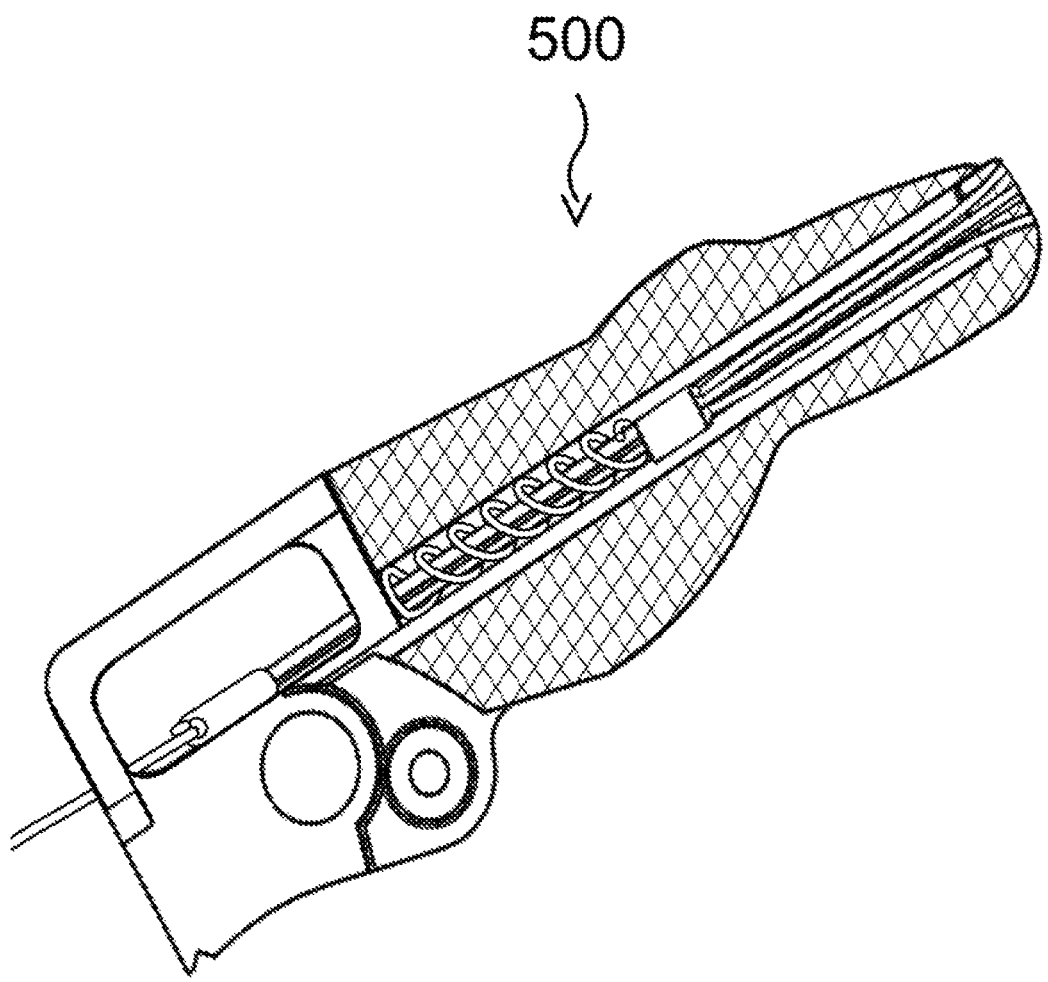
FIG. 21 is a cross sectional side view of the end effector of FIG. 19 in an undeployed position.

FIGS. 17-18 show a distal segment 400 of a pointer-finger according to another embodiment, i.e., bending tongs. In this embodiment, the distal segment 400 includes a block-shaped body 402 with two fork legs 420, 422 extended therefrom at the proximal end 424 of the distal segment 400. The distal segment 400 can be attached to a proximal segment such as the proximal segment 204 at the pivot point 426 on the fork legs. On the distal end, two tongs or jaws 406, 408 are attached to the body 402. The distal segment 400 is shaped similar to a pair of tweezers. Two tongs 406, 408 each may include a tweezer head 412, 414 and a tweezer leg 416, 418. The tweezer heads 412, 414 form a gripper. A rectangular block 410 is coupled with the two tweezer legs and slides about them. The tweezer legs 416, 418 taper off towards the distal end such that when the rectangular block 410 slides along the tweezer legs towards the body 402, the gripper is forced to close. The tongs can be open by the spring-back tension of a spring streel 430. The tongs 406, 408 are shown to be closed in FIG. 17 when the block 410 is pulled towards the body 402 by a actuation mechanism such as a cable 428. FIG. 18 shows the tongs 406, 408 in an open position.

FIGS. 19-22 show a distal segment 500 of a pointer-finger according to yet another embodiment i.e., a wire tongs. The distal segment 500 includes a finger-shaped body 502 having a hollow channel 506 within the body 502 that houses pre-bent wires 508 and a rear body 512 for housing the wires when retracted. The compression spring 510 is disposed around the wires 508 in the finger-shaped body 502. There may be at least three pre-bent wires in the channel. The ends of the wire, when extended, shape like a claw and function as a gripper. This end effector, i.e., the gripper, is actuated with an interconnect (cable, linkage, chain) routed within the finger-shaped body. In the embodiment illustrated in FIGS. 19-21, a cable 514 is used as an interconnect. When the tension is released, the compression spring applies force on the wires causing the wires to extend from the fingertip 516 to become a gripper. As tension is applied when pulling on the cable 514, the wires are retracted, causing the gripper to grasp the object and secure the object in place. The proximal end 504 of the distal segment 500 may be configured to be attached to a proximal segment such as the proximal segment 204 or may also be configured to be attached to a prosthetic palm as a finger.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

The invention claimed is:

1. A prosthetic digit, comprising:
   a main body having a proximal segment for attachment to a palm and a distal segment pivotally attached to a distal end of the proximal segment, the main body being flexed when the distal segment is pivoted relative to the proximal segment and the proximal segment is pivoted relative to the palm; and
   a terminal gripper at a distal end of the distal segment of the main body for enabling fine-motor grasping skills, the terminal gripper having at least two tongs movable relative to one another for gripping an object therebetween.

2. The prosthetic digit of claim 1, further comprising an actuation mechanism for driving the terminal gripper.

3. The prosthetic digit of claim 2, wherein the actuation mechanism is body-powered by movement of a user's body part.

4. The prosthetic digit of claim 2, wherein the actuation mechanism is electrically-powered.

5. The prosthetic digit of claim 1, wherein the prosthetic digit has a gripping mode and a flexion mode, in the gripping mode, the at least two tongs of the terminal gripper being able to move relative to one another while the main body being not able to flex, and in the flexion mode, the main body being able to flex while the at least two tongs of the terminal gripper being not able to move relative to one another.

6. The prosthetic digit of claim 5, further comprising a mode switch for switching between the flexion mode and the gripping mode.

7. The prosthetic digit of claim 6, wherein the mode switch is a lock for enabling/disengaging the gripping mode/the flexion mode.

8. The prosthetic digit of claim 5, further comprising an interconnect element, wherein the actuation mechanism is operable by applying/releasing tension to the interconnect element, which drives the tongs to open/close or close/open in the gripping mode and drives the to flex in the flexion mode.

9. The prosthetic digit of claim 8, wherein the interconnect element is a cable, a linkage or a chain.

10. The prosthetic digit of claim 1, wherein one of the at least two tongs is stationary and the other one of the at least two tongs is configured to pivot relative to the stationary tong.

11. The prosthetic digit of claim 1, further comprising a linkage, a central rack and two pinions, wherein the tongs are part of the linkage and actuated by the central rack and the two pinions.

12. The prosthetic digit of claim 1, wherein the tongs each include a head and a tapering leg, further comprising a block slidably coupled with the legs such that the tongs open or close when the block slides along the legs.

13. The prosthetic digit of claim 1, wherein the tongs are each shaped like a wire claw such that the terminal gripper has a plurality of wires for gripping.

14. The prosthetic digit of claim 1, wherein the terminal gripper has at least three tongs.

15. The prosthetic digit of claim 1, wherein the tongs are made from or covered with a textured material preventing slipping.

16. The prosthetic digit of claim 1, wherein each of the tongs are notched and cooperate to form a notch when closed.

17. The prosthetic digit of claim 1, wherein the prosthetic digit is a prosthetic finger digit.

18. A prosthetic digit, comprising:
    a main body; and
    a terminal gripper at an end of the main body for enabling fine-motor grasping skills, the terminal gripper having at least two tongs movable relative to one another, the at least two tongs both being movable.

19. The prosthetic digit of claim 18, further comprising an actuation mechanism for driving the terminal gripper.

20. The prosthetic digit of claim 19, wherein the actuation mechanism is body-powered by movement of a user's body part or is electrically-powered.

21. The prosthetic digit of claim 18, wherein the tongs are made from or covered with a textured material preventing slipping.

22. The prosthetic digit of claim 18, wherein each of the tongs are notched and cooperate to form a notch when closed.

23. The prosthetic digit of claim 18, wherein the prosthetic digit is a prosthetic finger digit.

24. A prosthetic digit, comprising:
    a main body;
    a terminal gripper at an end of the main body for enabling fine-motor grasping skills, the terminal gripper having at least two tongs movable relative to one another; and
    an actuation mechanism for driving the terminal gripper and gripping an object by with the at least two tongs.

25. The prosthetic digit of claim 24, wherein one of the at least two tongs is stationary and the other one of the at least two tongs is configured to pivot relative to the stationary tong.

26. The prosthetic digit of claim 24, wherein the actuation mechanism is body-powered by movement of a user's body part or is electrically-powered.

27. The prosthetic digit of claim 24, wherein the tongs are made from or covered with a textured material preventing slipping.

28. The prosthetic digit of claim 24, wherein each of the tongs are notched and cooperate to form a notch when closed.

29. The prosthetic digit of claim 24, wherein the prosthetic digit is a prosthetic finger digit.

30. A prosthetic hand, comprising:
   a palm;
   a thumb; and
   a plurality of fingers;
   one of the plurality of fingers comprising;
      a main body; and
      a terminal gripper at an end of the main body for enabling fine-motor grasping skills, the terminal gripper having at least two tongs movable relative to one another.

* * * * *